United States Patent
Henshaw

(10) Patent No.: US 7,322,941 B2
(45) Date of Patent: Jan. 29, 2008

(54) ARTERIAL SYRINGE SAFETY VENT

(75) Inventor: Robert J Henshaw, Newnan, GA (US)

(73) Assignee: ModalWorks Inc., Newnan, GA (US)

( * ) Notice: Subject to any disclaimer, the term of this patent is extended or adjusted under 35 U.S.C. 154(b) by 0 days.

(21) Appl. No.: 11/376,649

(22) Filed: Mar. 15, 2006

(65) Prior Publication Data

US 2007/0060841 A1    Mar. 15, 2007

Related U.S. Application Data

(63) Continuation-in-part of application No. 11/226,888, filed on Sep. 13, 2005.

(51) Int. Cl.
- *A61B 5/00* (2006.01)
- *A61B 19/00* (2006.01)
- *B65D 81/00* (2006.01)
- *A61M 5/00* (2006.01)
- *A61M 5/32* (2006.01)

(52) U.S. Cl. .................. 600/578; 604/110; 604/415

(58) Field of Classification Search ............... 600/573, 600/576–579; 604/415, 263, 88, 122, 198, 604/192, 110; 435/283.1, 2, 238; 424/529; 530/415; 206/366

See application file for complete search history.

(56) References Cited

U.S. PATENT DOCUMENTS

| | | | |
|---|---|---|---|
| 4,775,376 A * | 10/1988 | Strung | 604/415 |
| 4,982,842 A | 1/1991 | Hollister | 206/365 |
| 5,125,415 A | 6/1992 | Bell | 128/766 |
| 5,147,309 A * | 9/1992 | Hemmerich et al. | 604/122 |
| 5,342,320 A | 8/1994 | Cameron | |
| 5,554,127 A | 9/1996 | Crouther et al. | 604/192 |
| 6,491,667 B1 | 12/2002 | Keane et al. | 604/192 |
| 7,037,642 B2 * | 5/2006 | Hei | 435/2 |

* cited by examiner

Primary Examiner—Max F. Hindenburg
Assistant Examiner—Brian Szmal
(74) Attorney, Agent, or Firm—Lewinski Law Group LLC

(57) ABSTRACT

An improved arterial syringe safety vent is dually optimized for needle safety and arterial blood degassing efficiency. The safety vent of the invention includes a housing, a needle lock to capture a needle, and a venting portion comprising a hydrophilic filter. The needle lock of the invention is adapted to lock a needle tip between a membrane and a venting potion to prevent accidental needle stick. In en exemplary embodiment the safety vent of the invention engages a needle capture device in a manner that allows movement of the housing in relation to the needle capture device so that the tip of a needle captured by the needle capture device can be locked in a position that prevents exposure of the needle tip. The safety vent of the invention is self-supporting to permit single-handed operation.

20 Claims, 11 Drawing Sheets

ARTERIAL SYRINGE SAFETY VENT

CROSS REFERENCE TO RELATED APPLICATION

This application is a continuation-in-part of U.S. patent application Ser. No. 11/226,888, filed on Sep. 13, 2005, for an "Arterial Syringe Safety Vent".

FEDERALLY SPONSORED RESEARCH

Not Applicable

SEQUENCE LISTING OR PROGRAM

Not Applicable

BACKGROUND—FIELD OF THE INVENTION

The present invention relates to the sample collection and preparation of arterial blood for subsequent blood gas analysis, specifically to a more efficient and safer blood degassing procedure for the arterial blood sample prior to analysis.

BACKGROUND—DISCUSSION OF PRIOR ART

Arterial blood samples are used to determine the amount of blood gas (oxygen and carbon dioxide) or variables that depend upon the blood gas levels in a patient's blood. Typically, a blood sample is collected from a patient via an arterial syringe. During the course of a routine sample collection, the arterial syringe's needle is inserted into a patient's artery. Once the needle is inserted, the design of the arterial syringe allows for a patient's blood to flow into the syringe. This filling process usually occurs until the blood reaches the syringe's stopple or plunger. Once filled, the syringe's needle is removed from the patient's artery.

With the patient's blood sample now located in the syringe's barrel, it becomes very important to expel any entrapped air bubbles that might have been captured and/or created during the sample collection process. The air bubbles can typically be located at various locations in the syringe (at or near the syringe's stopple, needle, or needle hub). Nonetheless, it is highly desirable to purge the arterial blood sample of these external air bubbles in an effort to maintain the sample's integrity.

U.S. Pat. No. 5,554,127 to Crouther et al disclose a device and method for degassing a drawn blood sample. The '127 patent describes a device composed of a thimble shaped rigid plastic cap further containing a hydrophilic porous plastic core positioned on the thimble's interior. There are several disadvantages of this system. In practice, a user of this device is required to pierce the hydrophilic porous plastic core with the syringe's needle in order to initiate the degassing procedure. If the needle's gage is large, this requirement can be difficult to perform. Additionally, because the core used in the thimble cap is a porous plastic, the core can shed plastic particles that can subsequently get lodged into syringe's needle. This porous plastic particulate can potentially damage subsequent analytical equipment or could lead to unpredictable discharge flow rates from a syringe's partially clogged needle.

The '127 patent further teaches that the syringe, thimble cap, and blood sample should be inverted (needle pointing upward) at the start of the degassing process. In this arrangement, the primary venting material, i.e., the hydrophilic porous plastic core is located at a point lower than the tip of the syringe's needle tip. As the needle's plunger is pressed, blood will immediately flow down towards the hydrophilic porous plastic core and will subsequently wick into the hydrophilic porous plastic core. Once the core's pores are filled with fluid, fluid/gas from the syringe will no longer pass into the thimble cap. In short, this required syringe orientation will dramatically limit the amount of fluid/gas that can be purged from the syringe and will likely not provide adequate degassing of the drawn blood sample.

The use of this device also introduces healthcare providers to additional blood exposure risks. Following the degassing process with the thimble cap, the '127 patent teaches that healthcare providers are required to remove the needle/ needle hub and thimble cap from the syringe. Then, the '127 patent instructs the healthcare provider to cover the open end of the syringe with an auxiliary syringe cap to prevent the sample's exposure to air. Following the removal of the thimble cap and prior to the assembly of the auxiliary syringe cap, healthcare providers can be exposed to the blood located in the syringe, which presents obvious safety hazards.

Similarly, the procedure of removing the needle/needle hub and thimble cap from the arterial syringe and subsequently capping the arterial syringe is a two handed operation. Healthcare workers would benefit from an arterial blood degassing procedure that only requires one hand. If this option were available, the healthcare worker could use one hand to degas the arterial blood sample while using the second hand to assist with the patient's bandage at the needle's entry/exit point.

U.S. Pat. No. 5,125,415 to Bell discloses a popular device manufactured by Smith's Medical (Keene, N.H.). The '415 patent describes a syringe tip cap that is designed to fit onto the end of syringe following the sample collection routine. The main advantage of the '415 patent over the '127 patent involves the location of the hydrophilic vent material in the syringe tip cap. With the needle and tip cap positioned above the syringe's plunger, degassing of the arterial blood sample can occur without premature wetting of the tip cap's hydrophilic vent. As a result, a more complete degassing process is available with this design. However, the '415 patent like the '127 patent requires that the syringe's needle/needle hub assembly be removed prior to assembly of the tip cap onto the syringe. Therefore, like the '415 patent, the '127 patent allows for a time when blood is located in a non-capped syringe that can expose healthcare providers to potential risks. Further, the '415 patent falls short of providing the healthcare worker with a single-handed fluid degassing solution. Lastly, the '415 patent does not make any provisions for needle safety.

U.S. Pat. No. 4,982,842 to Hollister discloses a needle safety device also manufactured by Smith's Medical that is routinely sold in conjunction with the device described by the '415 patent The market presence of this device suggests its effectiveness as an efficient means to offer needle safety to healthcare workers, however, the device fails to integrate blood sample degassing functionality. Instead, users of the device regularly use the degassing device described in the '415 patent to purge gas from the blood sample.

U.S. Pat. No. 6,491,667 to Keane et all again disclose syringe tip caps for use with arterial syringes. However, like the previously discussed prior art, this patent also requires that the syringe's needle be removed prior to assembly of the tip cap. Therefore, this design also fails to provide needle safety and fluid degassing functionality in a singular device.

OBJECTS AND ADVANTAGES

Accordingly, several objects and advantages of my invention are to provide an improved arterial syringe degassing method and device that:
a. can be performed with only one hand;
b. incorporates needle safety functionality,
c. allows for efficient degassing of an arterial blood, and
d. offers the user with tactile and visual feedback with regards to degassing operation.

Still, further objects and advantages will become apparent from a consideration of the ensuing description and drawings.

SUMMARY

In accordance with the present invention, an arterial syringe safety vent is presented which is dually optimized for needle safety and blood degassing efficiency that can be operated with a single hand.

DRAWINGS

Drawing Figures

The arterial syringe safety vent will be best understood by reference to the following drawings in which.

REFERENCE NUMERALS IN DRAWINGS

Figure 1:
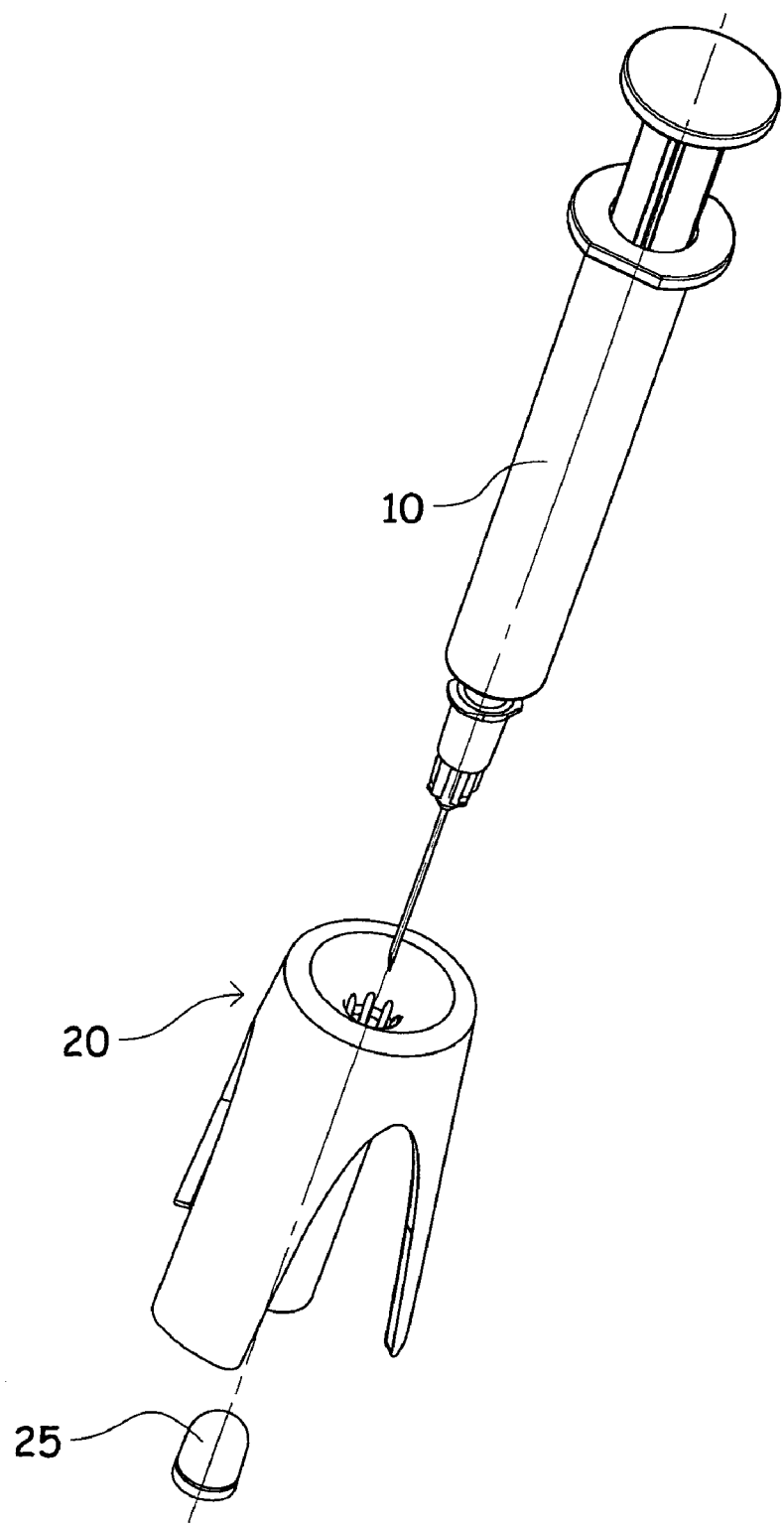
FIG. 1 is an exploded view of an exemplary embodiment of an arterial syringe safety vent shown with an arterial syringe.

10 Arterial syringe
11 Syringe plunger
12 Syringe barrel
13 Needle
14 Needle hub
15 Needle hub flutes
20 Arterial syringe safety vent
20a Arterial syringe safety vent (alternative embodiment)
20b Arterial syringe safety vent (second alternative embodiment)
21 Legs
22 Needle opening
23 Filter opening
24 Capture flutes
25 Filter
26 Gripping ring(s)
27 Penetrable membrane
28 Air Gap
40 Universal arterial syringe safety vent
41 Needle capturing clamshell
42 Locking joint
43 Leaf spring
44 Positioning Barb
45 Catch
51 Rails
52 Needle capture system
53 Hinge
54 Positioning catch

DETAILED DESCRIPTION

Description—FIG. 1-4, Preferred Embodiment

Figure 2:
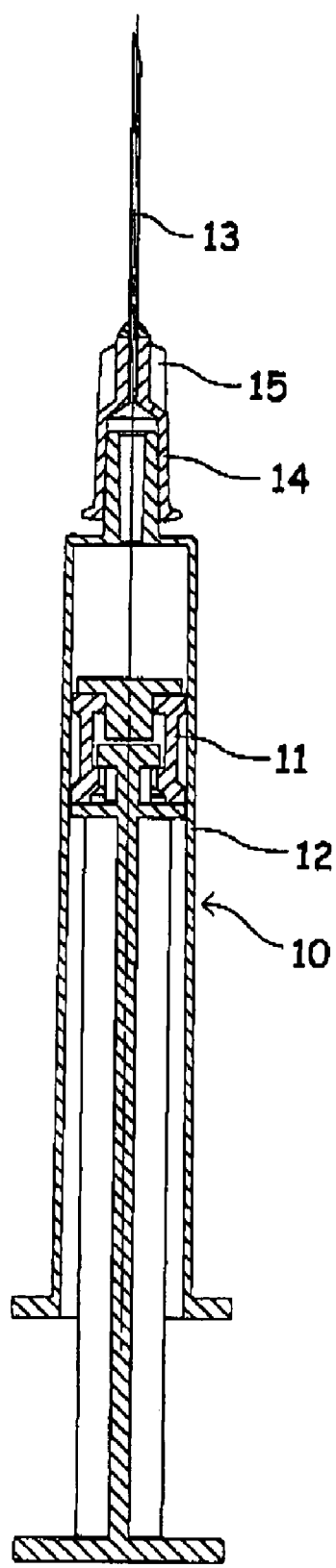
FIG. 2 is a cross sectional view of the prior art arterial syringe of FIG. 1.

FIG. 1 illustrates in exploded view arterial syringe 10 and arterial syringe safety vent 20. Arterial syringe 10 shown in FIG. 2 is of standard tubular design fitted with a plunger 11 slidably received therein so that the inside walls of the tube and the outer edge of plunger 11 produce a tight fit with the inner walls of syringe barrel 12. A needle assembly composed of needle 13 and needle hub 14 are attached to syringe's barrel 12 by means of a traditional slip lure lock (shown) or male-female lure lock (not shown). Extending away from the axis of needle hub 14 are four needle hub flutes 15 located in equal spacing around the perimeter of hub 14. The size, length, and profile of needle 13, needle hub 14, and hub flutes 15 are typical of those supplied by hypodermic needle manufacturers such as Kendall (a division of Tyco International, Princeton, N.J.), Terumo Medical Corporation (Somerset, N.J.), and Becton Dickinson (Franklin Lakes, N.J.).

Figure 3:
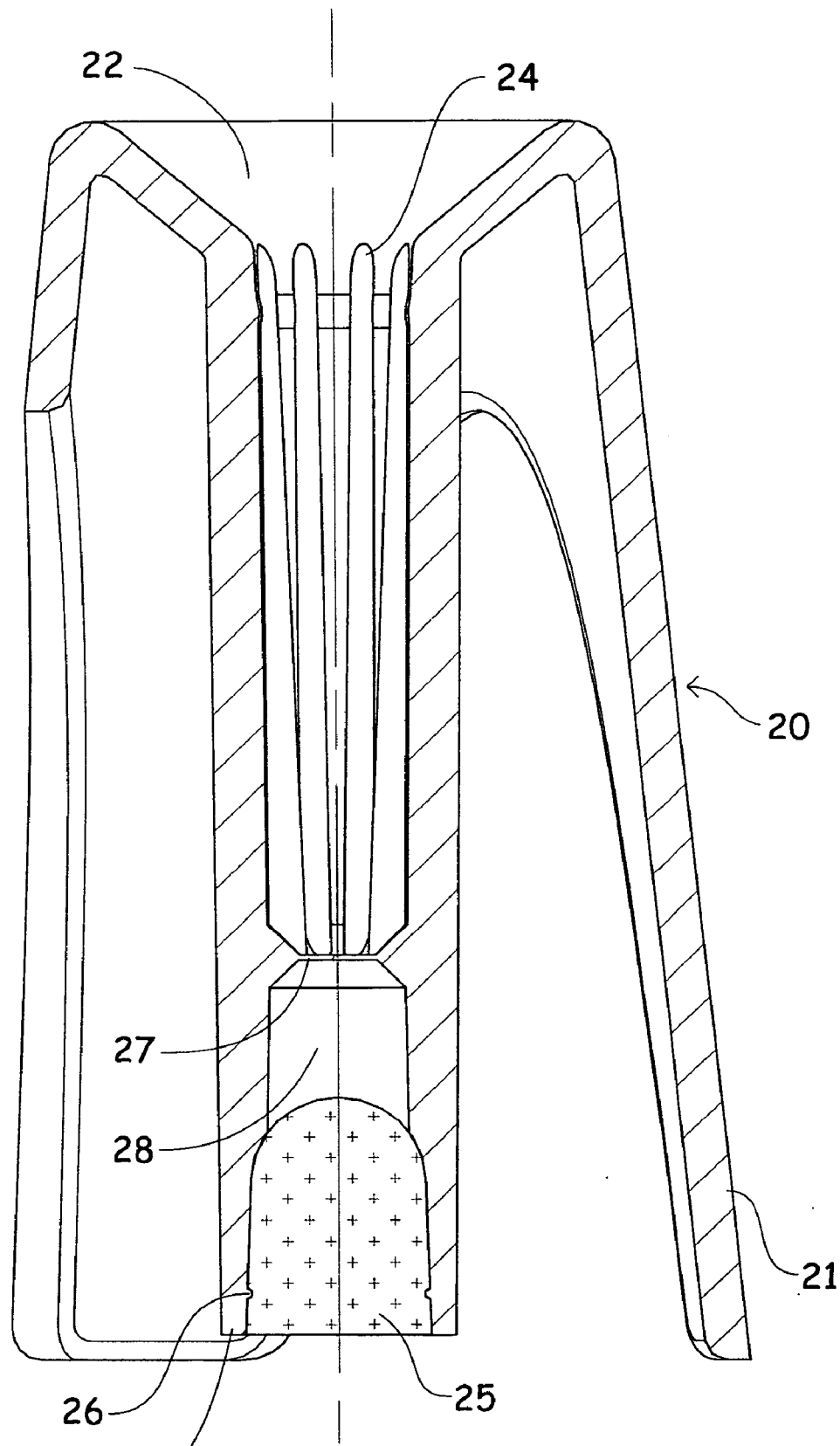
FIG. 3 is a cross sectional view of the arterial syringe safety vent of FIG. 1.

Arterial syringe safety vent 20 shown in FIG. 3 is preferably made from a clear injection moldable material such as styrene-butadiene-copolymer, available from Chevron Phillips Chemical (The Woodlands, Texas), and composes legs 21 that enable the base to rest on a horizontal surface. Located on opposing ends of arterial syringe safety vent 20 are needle opening 22 and filter opening 23. Capture flutes 24 are located in equal spacing around the perimeter of needle opening 22. The size, shape, and taper of these capture flutes 24 are sized to create an interference fit with arterial syringe flutes 15, FIG. 1.

Filter opening 23 is sized to receive filter 25. Preferably, the inner diameter of the filter opening 23 is approximately 0.010" less than the outside diameter of filter 25 to facilitate a press fit. Alternatively, one or multiple gripping ring(s) 26 can be added to further secure filter 25 in place.

Filter 25 is preferably made from a blend of any sinterable thermoplastic material (such as polyethylene) and a cellulose additive and comprises a nominal pore size less than 75 microns. Filter 25 is available from various porous plastic manufacturers such as Porex (Fairburn, Ga.), Micropore Plastics (Stone Mountain, Ga.), MA Industries (Peachtree City, Ga.).

Located between needle opening 22 and filter opening 23, arterial syringe safety vent 20 further incorporates penetrable membrane 27 and air gap 28 of sufficient volume to facilitate arterial blood collection during the degassing operation.

Figure 4:
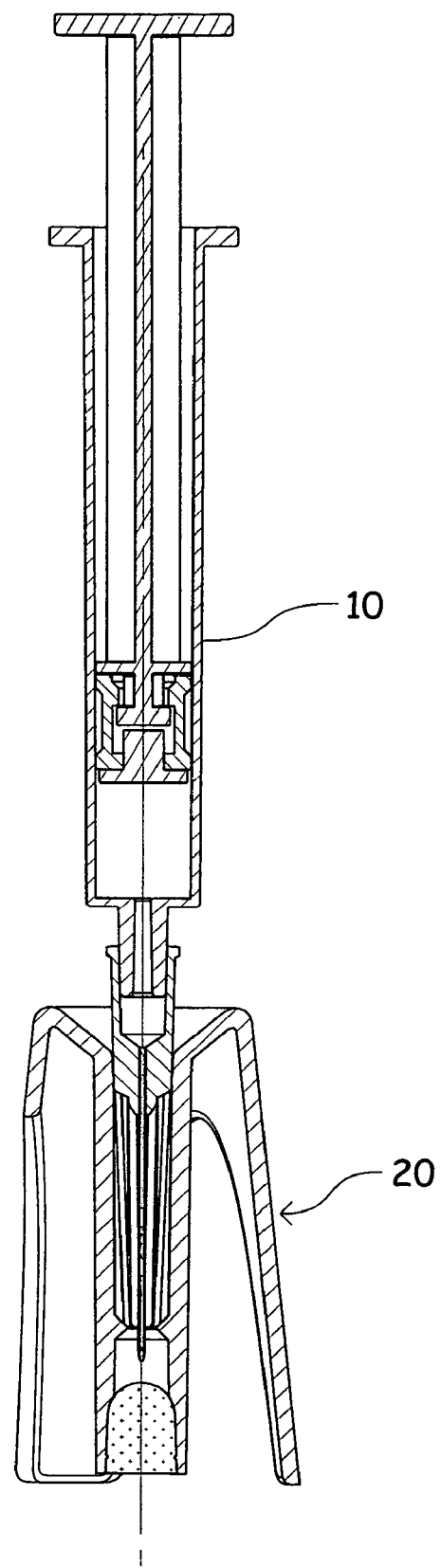
FIG. 4 is a cross sectional view of an arterial syringe safety vent shown with the arterial syringe of FIG. 2.

FIG. 4 is a cross sectional view of FIG. 1 that shows arterial syringe 10 captured and locked into arterial syringe safety vent 20.

Figure 5:
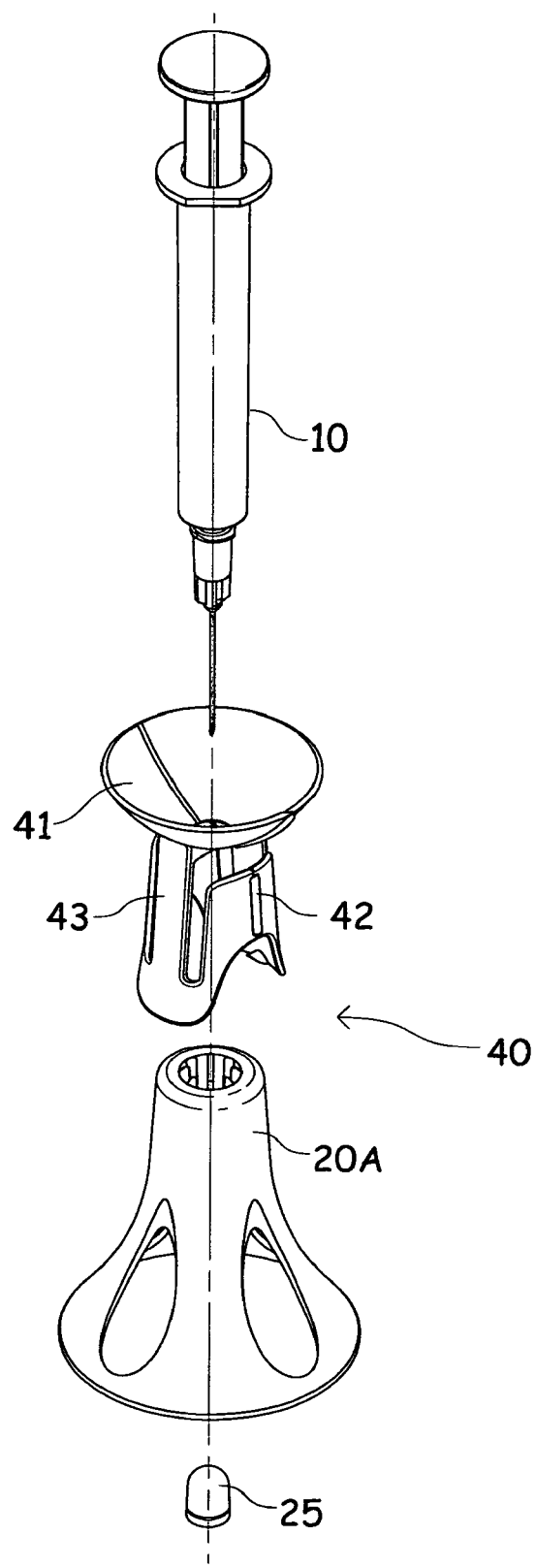
FIG. 5 is an exploded view of a further exemplary embodiment of an arterial syringe safety vent shown with the arterial syringe of FIG. 2.
Figure 6:
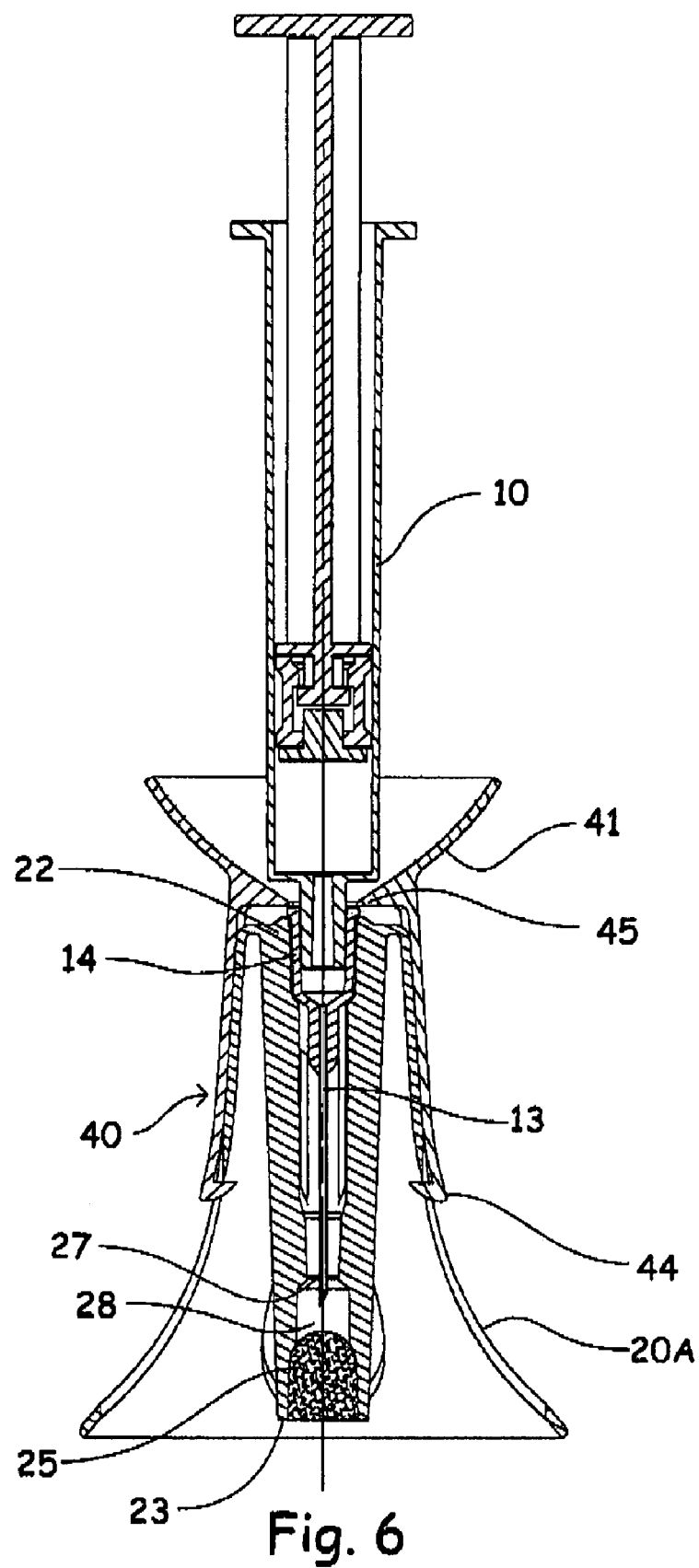
FIG. 6 is a cross-sectional view of the exemplary embodiment shown in FIG. 5.
Figure 7:
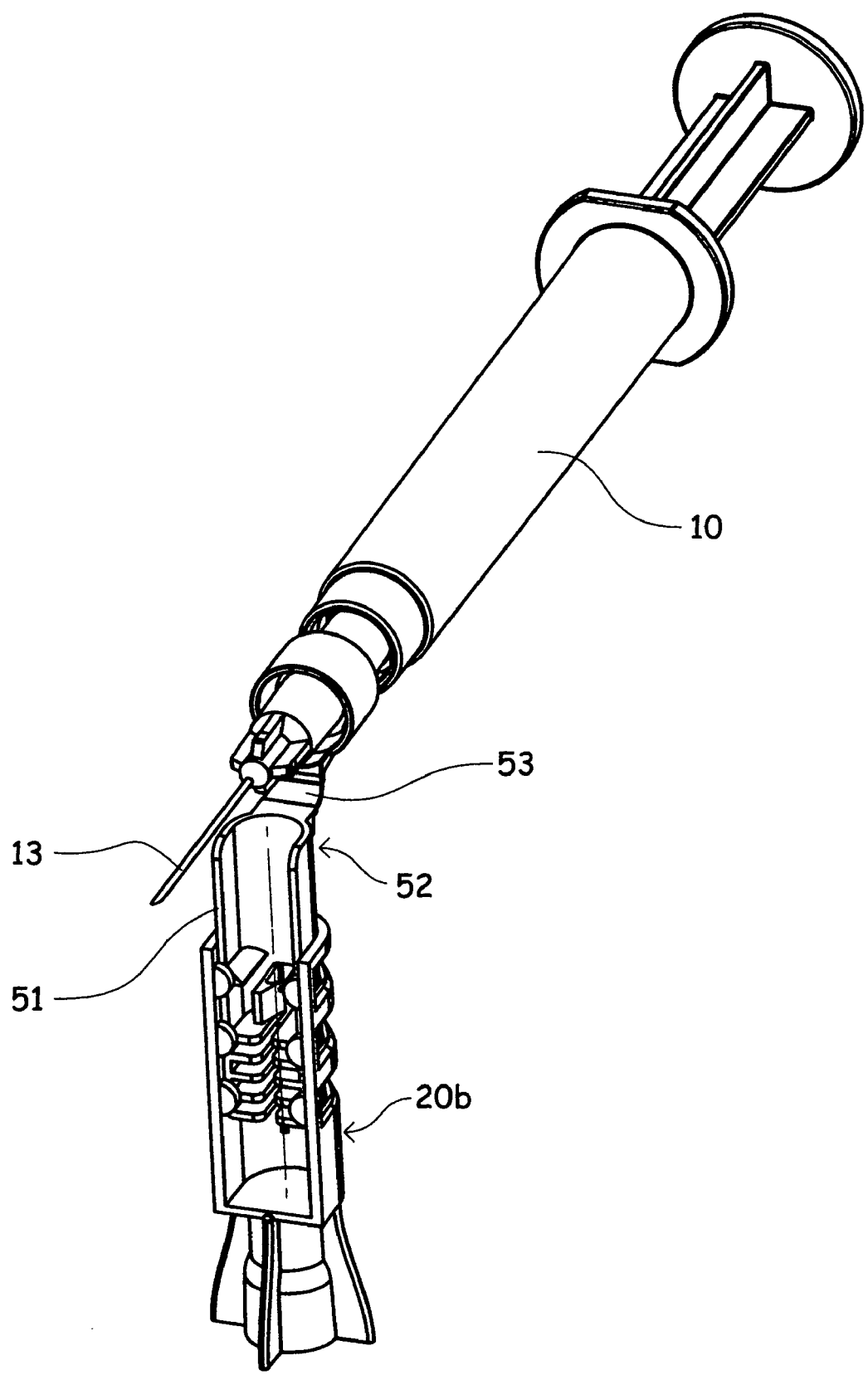
FIG. 7 shows a an exemplary embodiment of an arterial syringe safety vent.
Figure 8:
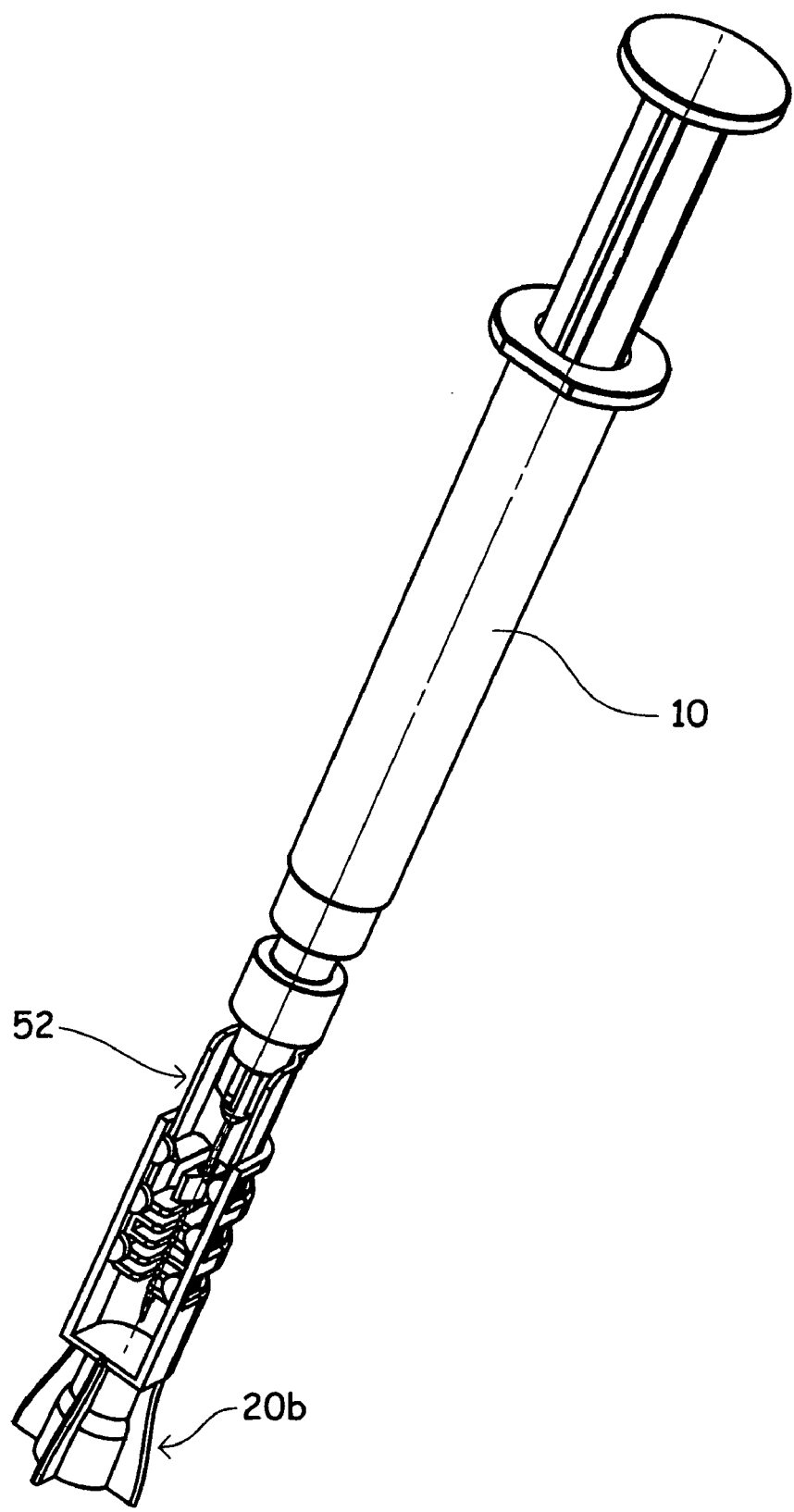
FIG. 8 depicts an embodiment of an arterial syringe apparatus of the present invention with a captured needle.

Description—FIG. 5-6, First Alternative Embodiment

Illustrated as a first alternative embodiment of this invention, FIG. 5 and FIG. 6 show arterial syringe 10 with an universal arterial syringe safety vent 40 in exploded and cross section view respectively. Universal arterial syringe safety vent 40 is composed of an arterial syringe safety vent 20a and a needle-locking clamshell 41 positioned around the perimeter of needle opening 22. Needle locking clamshell 41 is composed of two symmetrical halves fitted to one another by a locking joint 42 and further comprises leaf spring 43, positioning barb 44 and catch 45.

Description—FIG. 7-11, Second Alternative Embodiment

Illustrated as a second alternative embodiment of this invention,

FIG. 7-11 describe an arterial syringe safety vent 20b working in conjunction with a needle safety system such as the one manufactured by Smith's Medical (Keene, N.H.) described by U.S. Pat. No. 4,982,842. In this arrangement, arterial syringe safety vent 20b embodies the basic features of the previously described preferred embodiment, i.e., filter 25, penetrable membrane 27, air gap 28. However, this embodiment does not incorporate any needle capture functionality into the arterial syringe safety vent 20b. Instead, this embodiment adds blood sample degassing functionality to the needle capture system described in the '842 patent via rails 51 which facilitates movement of arterial syringe safety vent 20b in an axial direction relative to needle 13 and needle capture system 52.

Operation—FIGS. 1-4

A blood gas sample is first drawn from a patient and collected into arterial syringe 10. Using one hand, the healthcare worker can insert arterial syringe's needle 13 into needle opening 22 of arterial syringe safety vent 20. As needle 13 travels down arterial syringe safety vent 20, needle hub 14 will come into contact with capture flutes 24 and the tip of needle 13 will come into contact with penetrable membrane 27. As arterial syringe 10 is further depressed into arterial syringe safety vent 20, needle 13 will pierce and travel through penetrable membrane 27. Penetrable membrane 27 will subsequently create a seal around the outside diameter of needle 13. Shortly thereafter and as arterial syringe 10 is further depressed into arterial syringe safety vent 20, an interference fit occurring between needle hub flutes 15 and capture flutes 24 will lock arterial syringe 10 to arterial syringe safety vent 20.

Once secure in place, the healthcare worker positions arterial syringe 10 and arterial syringe safety vent 20 upright so that arterial syringe safety vent 20 is above arterial syringe 10 to gather air bubbles close to needle hub 14. Syringe plunger 11 can then be depressed to force the blood sample into air gap 28. As blood flows into air gap 28, the gas present in the arterial blood sample will vent through filter 25 while the blood begins to accumulate on penetrable membrane 27. As syringe plunger 11 is further depressed, the blood sample will fill air gap 28 towards filter 25. Eventually, as more blood is expelled from arterial syringe 10, the blood will fully occupy air gap 28 and come into contact with filter 25. Once the blood is in contact with filter 25, the pores of filter 25 will fill with fluid due to its hydrophilic properties (created by the cellulose additive). As the blood and the cellulose contained within filter 25 mix, the viscosity of the blood will increase thereby prohibiting additional fluid flow through filter 25. Once this occurs, air and fluid will cease to flow through filter 25 and the external air previously entrapped within the arterial blood sample will be purged.

Operation, First Alternative Embodiment—FIGS. 5-6

As was previously described, a blood gas sample is first drawn from a patient and collected into arterial syringe 10. Using one hand, the healthcare worker can insert needle 13 of arterial syringe 10 into needle opening 22 of universal arterial syringe safety vent 40. As needle 13 travels down arterial syringe safety vent 20a, needle hub 14 will come into contact with inner diameter of needle locking clamshell 41.

As needle hub 14 travels farther down needle opening 22, leaf springs 43 will allow the inner diameter of needle locking clamshell 41 to increase and catch 45 will be in contact with needle hub 14. Once needle hub 14 passes catch 45, the tension in leaf springs 43 will cause catch 45 to move towards its center, thus reducing the inner diameter of needle locking clamshell 41 to a distance less than the diameter of needle hub 14. In this position, needle locking clamshell 41 will effectively prevent removal of needle 13 and needle hub 14 from universal arterial syringe safety vent 40.

The remaining blood degassing operation associated with this alternative embodiment is identical to the previous described embodiment, i.e., the needle penetrates penetrable membrane, the needle is inverted, and the gas expelled from the collected blood sample.

Operation, Second Alternative Embodiment—FIGS. 7-11

Figure 9:
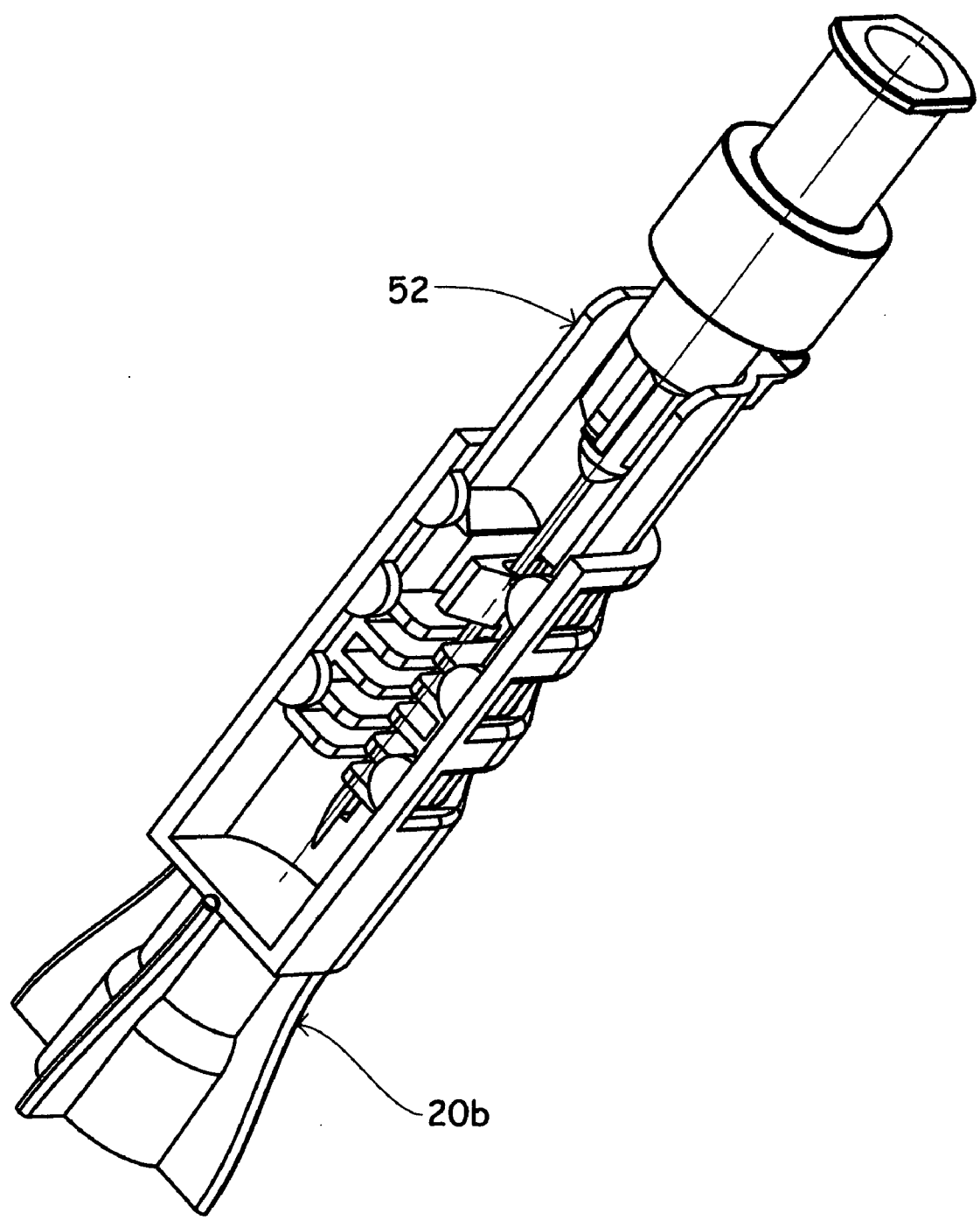
FIG. 9 shows an exemplary embodiment of the present invention.
Figure 10:
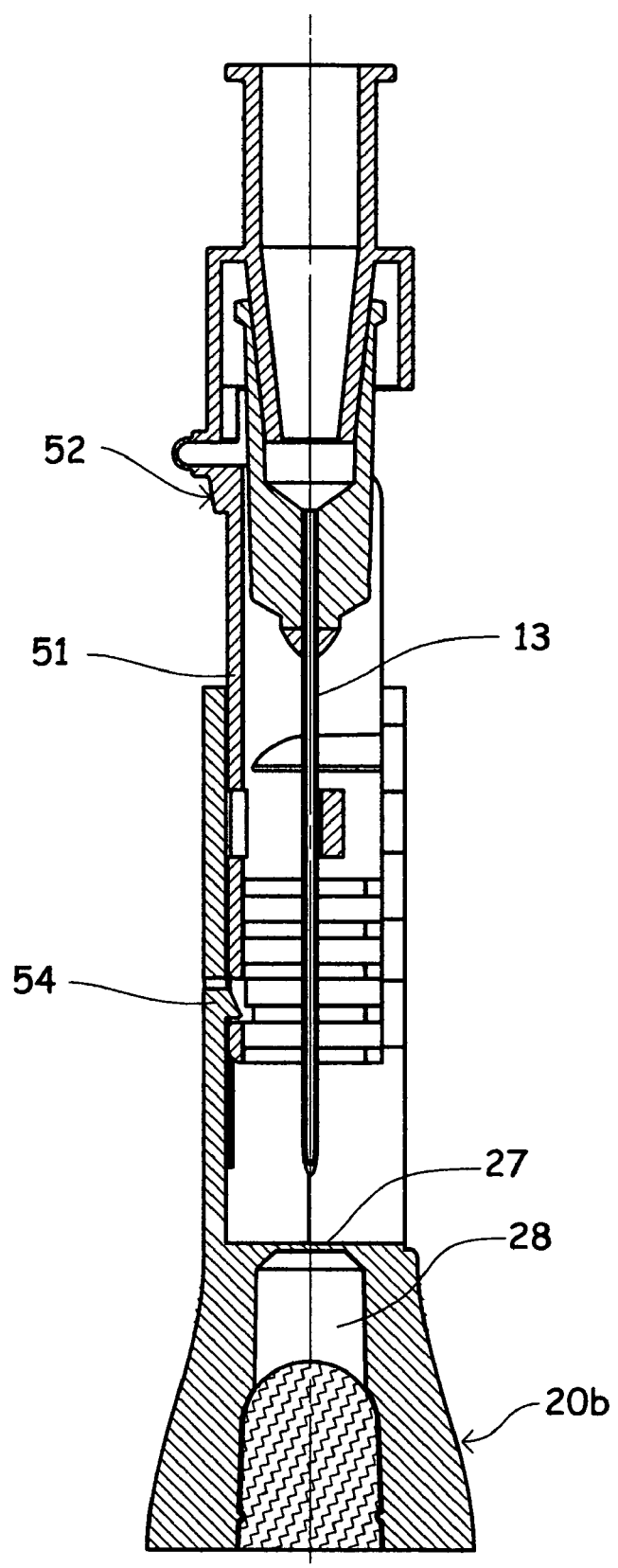
FIG. 10 shows a cross-sectional view of the embodiment shown in FIG. 9.
Figure 11:
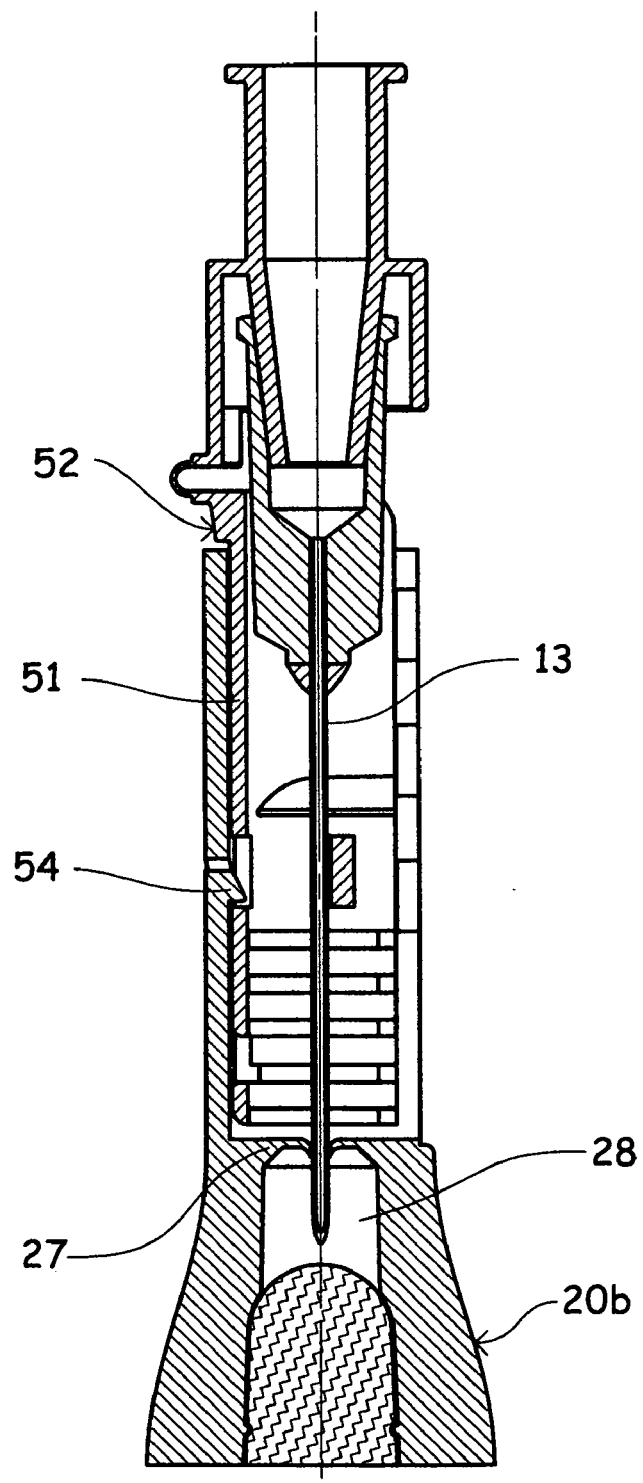
FIG. 11 shows a cross-sectional view of an exemplary embodiment of the invention engaging a needle capture device.

As was previously described, a blood gas sample is first drawn from a patient and collected into arterial syringe 10. Needle capture system 52 and arterial syringe safety vent 20b is then rotated about hinge 53 to capture needle as described by U.S. Pat. No. 4,982,842 (shown in FIG. 8). FIG. 9 shows the same needle capture orientation without arterial syringe 10 and FIG. 10 shows a cross section of FIG. 9. Once needle 13 is captured by needle capture system 52, arterial syringe safety vent 20b is slid towards needle 13 along rails 51. As the needle travels towards arterial syringe safety vent 20b, needle 13 will pierce penetrable membrane 27. Once pierced, the syringe safety vent 20b is further depressed until positioning catch 54 is engaged to secure arterial syringe safety vent 20b into final position relative to needle capture system 52. From this point, the remaining blood degassing operation associated with this second alternative embodiment is identical to the previous described embodiments.

CONCLUSION, RAMIFICATIONS, AND SCOPE

Thus the reader will see that the arterial syringe safety vent of the invention provides a highly efficient and safe degassing device that facilitates single-handed operation.

While my above description contains many specificities, these should not be construed as limitations, but rather as an exemplification of three embodiments thereof. Many other variations are possible that can be built upon the previously discussed arterial syringe safety vent featuring a penetrable membrane, air gap, and filter arrangement. For example, a custom syringe could be manufactured that improves needle capture efficiency. Such a custom syringe might incorporate one or multiple undercuts or bosses specially designed to lock onto a modified arterial syringe safety vent housing. Similarly, the undercut(s) or boss(es) of the custom syringe could be designed to facilitate a male-female thread arrangement to the arterial syringe safety vent.

Another variation to the basic design of this invention might feature a safety vent comprised of two different materials. For example, the vent's base could be molded from a standard polyethylene or polypropylene material while the penetrable membrane was molded from a thermoplastic elastomer, such as Santoprene (available from Advanced Elastomer System, LP, Akron, Ohio), to create a more pliable seal around the syringe's needle.

In yet another variation, manufacturing capabilities might dictate the arterial syringe safety vent production as an assembly from two separately manufactured components, i.e., the penetrable membrane might be independently molded and later affixed into the arterial syringe safety vent's base by means of traditional ultrasonic, mechanical entrapment, or adhesive/chemical bonding arrangement.

In short, there are numerous needle capture, material, and manufacturing variations that can be built off the basic platform of the current invention; accordingly, the scope of the invention should be determined not by the embodiments illustrated, but by the appended claims and their legal equivalents.

I claim:

1. An arterial syringe apparatus comprising:
a housing containing first and second opposing open ends;
a needle lock adapted to unreleasably capture a hypodermic needle;
a penetrable membrane; and
a venting means, consisting of a filter fixed between said second end and said penetrable membrane, said filter capable of preventing the flow of liquid through said second end;
wherein said needle lock is adapted to allow a needle's tip to pierce said membrane, after which a needle's tip is locked between said membrane and said venting means.

2. The device as recited in claim 1, wherein said filter is comprised of a sintered porous thermoplastic containing a cellulose additive.

3. The arterial syringe apparatus of claim 1, wherein said needle lock comprises at least one capture flute adapted to provide an interference fit with at least one needle hub flute of an arterial syringe.

4. The arterial syringe apparatus of claim 1, wherein said needle lock comprises a clamshell needle lock.

5. The arterial syringe apparatus of claim 1, wherein said penetrable membrane is provided between said needle lock and said second end.

6. The arterial syringe apparatus of claim 1, wherein said venting portion is provided between said penetrable membrane and said second end.

7. The arterial syringe apparatus of claim 1, wherein said housing is adapted to be self-supporting on a horizontal surface so that said first end is adapted to receive a downwardly oriented hypodermic needle of an arterial syringe.

8. The arterial syringe apparatus of claim 7, wherein said housing comprises at least one leg.

9. The arterial syringe apparatus of claim 1, wherein said housing is adapted to receive a needle capture device and allow movement of said housing along said received needle capture device.

10. The arterial syringe apparatus of claim 9, wherein said housing is adapted to engage and unreleasably capture said needle capture device.

11. An arterial syringe apparatus comprising:
a housing containing first and second opposing ends;
a venting naeans; and
a penetrable membrane;
wherein said housing is adapted to couple with a needle capture device to permit movement of said housing in relation to said needle capture device to allow a needle unreleasable captured by said needle capture device to penetrate said penetrable membrane, so that after piercing the membrane a needle's tip is locked between said membrane said venting means.

12. The arterial syringe apparatus of claim 11, wherein said housing is adapted to engage and unreleasably capture said needle capture device.

13. The arterial syringe apparatus of claim 11, wherein said venting means is provided between said penetrable membrane and said second opposing end.

14. The arterial syringe apparatus of claim 11, wherein said venting means comprises a filter capable of preventing the flow of liquid through said second end.

15. The arterial syringe apparatus of claim 11, wherein said venting means comprises a hydrophilic filter.

16. An arterial syringe degassing device, comprising:
a needle capture means adapted to unreleesably capture a hypodermic needle of an arterial syringe;
a housing;
a penetrable membrane; and
a venting portion,
wherein said housing is adapted to couple with said needle capture means in a manner that allows movement in relation to said needle capture means so that a needle secured within said needle capture means can penetrate said penetrable membrane, so that after said penetration a needle's tip is locked between said membrane and said venting portion.

17. The arterial syringe degassing device of claim 16, wherein said housing is adapted to engage and unreleasably capture said needle capture means.

18. The arterial syringe degassing device of claim 14, wherein said housing comprises first and second opposing ends.

19. The arterial syringe degassing device of claim 16, wherein said venting portion comprises a filter which prevents the flow of fluid through said second end.

20. The arterial syringe degassing device of claim 16, wherein said venting portion comprises a hydrophilic filter.

* * * * *